United States Patent [19]

Silvian

[11] Patent Number: 5,562,713
[45] Date of Patent: Oct. 8, 1996

[54] BIDIRECTIONAL TELEMETRY APPARATUS AND METHOD FOR IMPLANTABLE DEVICE

[75] Inventor: Sergiu Silvian, La Crescenta, Calif.

[73] Assignee: Pacesetter, Inc., Sylmar, Calif.

[21] Appl. No.: 375,311

[22] Filed: Jan. 18, 1995

[51] Int. Cl.$^6$ ........................................ A61N 1/37
[52] U.S. Cl. .................. 607/32; 607/60; 128/903
[58] Field of Search .................... 128/697, 903; 607/27, 30, 31, 32, 59, 60

[56] References Cited

U.S. PATENT DOCUMENTS

| | | | |
|---|---|---|---|
| 5,058,581 | 10/1991 | Silvian | 128/419 PG |
| 5,107,833 | 4/1992 | Barsness | 128/419 PT |
| 5,292,343 | 3/1994 | Blanchette et al. | 607/32 |
| 5,324,315 | 6/1994 | Grevious | 607/60 |
| 5,476,488 | 12/1995 | Morgan et al. | 607/32 |

Primary Examiner—William E. Kamm
Attorney, Agent, or Firm—Malcolm J. Romano; Lisa P. Weinberg

[57] ABSTRACT

An improved telemetry system for telemetering data from an implantable device such as a heart pacemaker to an external device with minimum energy consumption. The external device first sweeps its receiver across a predetermined frequency band, e.g., the fm broadcast band of 88 MHz to 108 MHz, to determine the particular frequency having the lowest ambient electromagnetic noise level, which it deems the optimum frequency for the telemetry to occur. The external device's transmitter then commands the pacemaker to telemeter a predetermined start signal at a succession of frequencies that sweep across that same frequency band, while the external device's receiver remains tuned to the optimum frequency. Eventually, the external devices receiver will receive the start signal and the external device thereupon will command the pacemaker to thereafter remain at its current frequency for the subsequent telemetry of data. Thus, the pacemaker is effectively tuned to the optimum frequency without the need for the pacemaker to incorporate an elaborate frequency synthesizer and without the need to draw excessive energy from the limited supply available so as to overcome interference at the operating frequency.

17 Claims, 2 Drawing Sheets

BIDIRECTIONAL TELEMETRY APPARATUS AND METHOD FOR IMPLANTABLE DEVICE

BACKGROUND OF THE INVENTION

This invention relates generally to implantable devices such as heart pacemakers and, more particularly, to telemetry apparatus and methods for use in transmitting data from such implantable devices.

Implantable devices of this kind are becoming increasingly sophisticated and now are commonly configured to transmit, or telemeter, large amounts of data to an external device, commonly called a programmer. In the case of a heart pacemaker, for example, it is frequently desired to transmit data representing the real time electrocardiogram (ECG) signal from one or more chambers of the heart and, in addition, to transmit other data accumulated over time in an internal memory.

Data of this kind is preferably telemetered at a data rate of at least 8000 bits per second, which is most readily achievable if the pacemaker includes an antenna external to the pacemaker's case. Such a telemetry system is disclosed in U.S. Pat. No. 5,058,581, which is incorporated by reference. In the disclosed telemetry system, a carrier frequency in the range of 10 to 300 MHz is considered to be suitable.

As is well known, implanted devices of this kind use a low-energy battery and, consequently, any telemetry apparatus should consume very low energy. This low-energy requirement effectively precludes the use of a crystal-controlled oscillator and transmitter output stage for driving the antenna. This is because, after implantation, the connector/lead capacitance will increase by an uncontrolled amount, which detunes the transmitter output stage and reduces the transmitted power. Further, extraneous electromagnetic noise sources might sometimes be present at the transmitter frequency, which interferes with the telemetered signal and requires a higher transmitter power to be used.

It should, therefore, be appreciated that there is a need for an improved telemetry apparatus, and related method, for transmitting data from an implantable device such as a heart pacemaker with minimal use of the limited electrical energy available. The present invention fulfills this need.

SUMMARY OF THE INVENTION

This invention is embodied in an improved telemetry apparatus, and related method, for effectively telemetering data from an implantable device to an external device, with very low energy consumption, even in the presence of one or more extraneous electromagnetic noise sources. The implantable device includes a transmitter and a receiver, which are operable at a selected frequency located within a predetermined frequency range, e.g., the fm broadcast band of 88 MHz to 108 MHz. The external device likewise includes a transmitter and receiver, operable at a selected frequency within the same frequency range. The external device initially determines a particular optimum frequency within the range, at which ambient electromagnetic noise from other sources is at a low level, and the transmitter of the implantable device is then commanded to transmit a predetermined start signal at a succession of frequencies within the range. While these successive start signals are being transmitted, the receiver of the external device is tuned to the optimum frequency that was previously determined, and the received signal is monitored until the predetermined start signal has been received. When it has been, the implantable device is commanded to remain at its current frequency, which should be at or near the optimum frequency. Telemetry of data, thereafter, can occur at that frequency with minimal interference from extraneous noise sources and, consequently, with minimum transmitted power.

In a more detailed feature of the invention, the optimum frequency is determined by sweeping the frequency of the external device's receiver across the predetermined frequency range and measuring the strength of the received eletromagnetic energy at each of a succession of discrete frequencies, and by then selecting as the optimum frequency the particular frequency at which the strength of the received eletromagnetic energy is lowest. Further, the transmitter of the implantable device is commanded to begin transmitting the succession of start signals by having the receiver of the implantable device tuned to a predetermined park frequency, e.g., a frequency at one end of the predetermined frequency range, and by causing the transmitter of the external device to transmit a predetermined command signal to the implantable device at that park frequency.

In another more detailed feature of the invention, the implantable device, upon receipt of the predetermined command signal from the external device, transmits the predetermined start signal at a succession of frequencies that sweeps uniformly across the predetermined frequency range, in discrete frequency steps. This is conveniently accomplished using a transformer and shunt varactor, along with means for generating a staircase voltage signal for application to the varactor. The implantable device thus is free of a crystal-controlled oscillator for use with its transmitter and receiver.

Other features and advantages of the present invention should become apparent from the following description of the preferred embodiment, taken in conjunction with the accompanying drawings, which illustrate, by way of example, the principles of the invention.

DESCRIPTION OF THE PREFERRED EMBODIMENT

Figure 1:
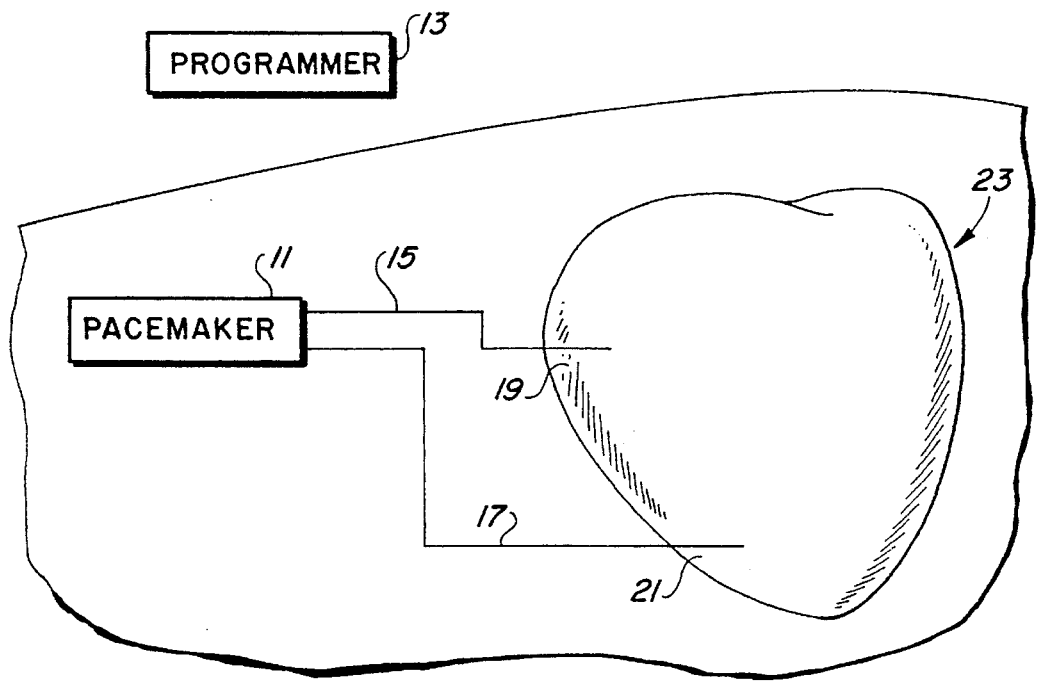
FIG. 1 is a schematic drawing of an implanted heart pacemaker configured in accordance with the invention to telemeter data, using its lead as an antenna, to an external device, or programmer.
Figure 2:
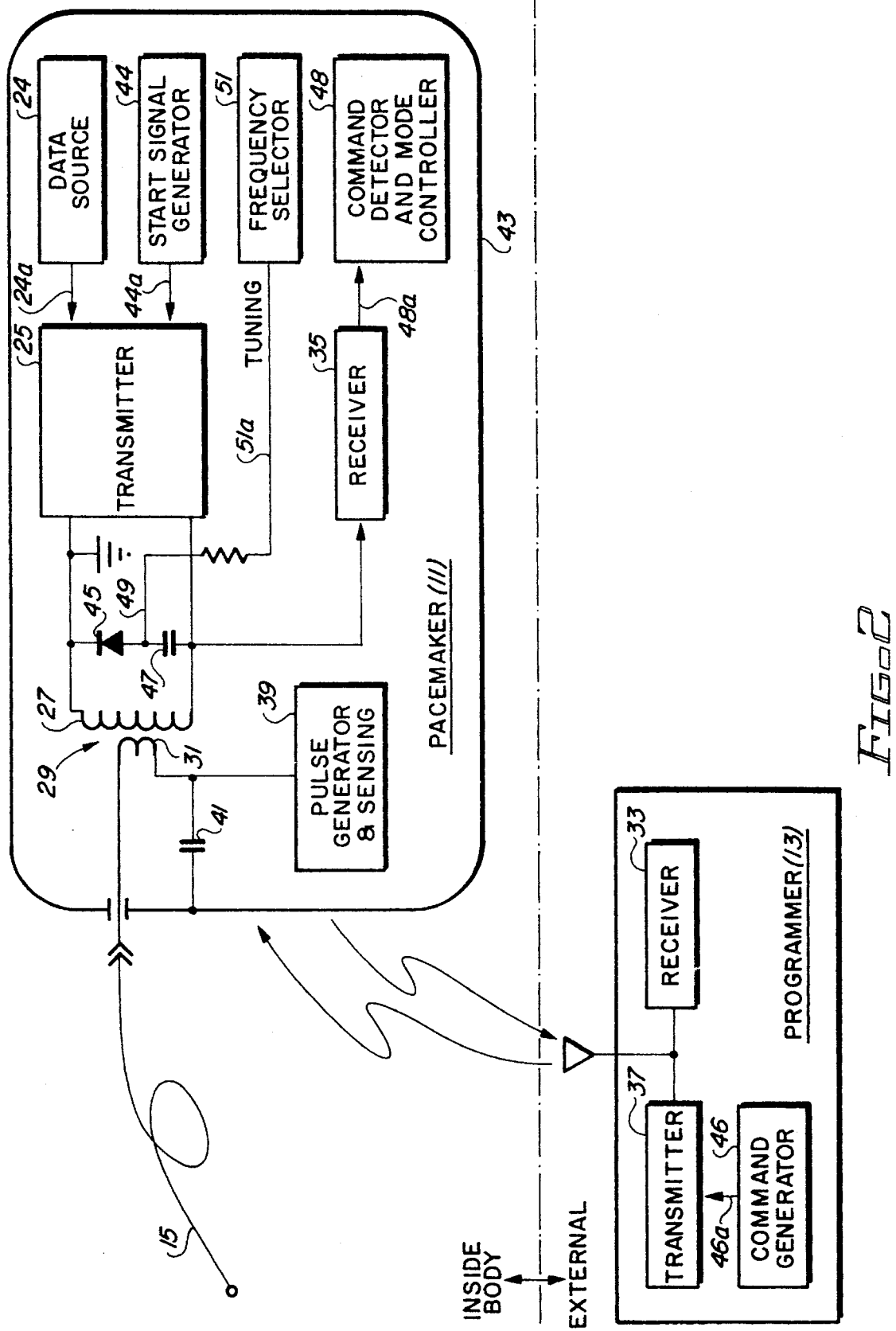
FIG. 2 is a simplified block diagram of the telemetry system of the invention, including a transmitter and a receiver in both the implanted pacemaker and the external device, or programmer.

With reference now to the drawings, and particularly to FIGS. 1 and 2, there is shown an apparatus for telemetering data from an implanted heart pacemaker 11 to an external device, or programmer 13. Electrical leads 15 and 17 connect the pacemaker to the right auricle 19 and right ventricle 21, respectively, of a heart 23. The leads carry stimulus signals from the pacemaker to the heart when a stimulation is required, and also carry electrocardiogram (ECG) signals from the heart to the pacemaker, for suitable processing and telemetering to the programmer.

The pacemaker 11 is configured to accumulate data in an internal memory, or data source 24, relating to the pacemaker's operation, such as the occurrences of detected irregularities in the ECG signals supplied to it and the occurrences of stimulus signals it produces for transmission over the leads 15 and 17 to the heart 23. This data periodically is retrieved from the data source and telemetered to the programmer 13. In particular, a transmitter 25 in the pacemaker retrieves the data via 24a and modulates an rf carrier in accordance the data and couples the modulated carrier signal to the primary winding 27 of a step-down transformer 29. The secondary winding 31 of the transformer is connected directly to the electrical lead 15, such that the lead functions as an antenna to radiate the signal to a receiver 33 in the programmer 13. A pacemaker receiver 35 also is connected to the primary winding, for receiving programming data, etc., from a transmitter 37 in the programmer. The carrier frequency is, in the preferred embodiment, selected to be in the fm broadcast band of 88 MHz to 108 MHz.

Although not directly related to the telemetry apparatus of the invention, a conventional pulse generator and sensing device 39, for both sensing ECG signals and generating any required stimulus signals, also is connected via the secondary winding 31 of the transformer 29 to the lead 15. A capacitor 41 couples the side of the secondary winding opposite the lead 15 to the pacemaker's grounded case 43.

It is, of course, desirable for the pacemaker 11 to telemeter data with as little consumed energy as possible. At the same time, however, an efficient telemetry of data at low power levels cannot be reliably achieved if extraneous sources of interfering electromagnetic noise are present at or near the telemetry frequency. The pacemaker and the programmer 13, therefore, are configured to implement a prescribed preparatory procedure that ensures that the telemetry occurs at a frequency having minimal interference from such extraneous sources.

Figure 3:
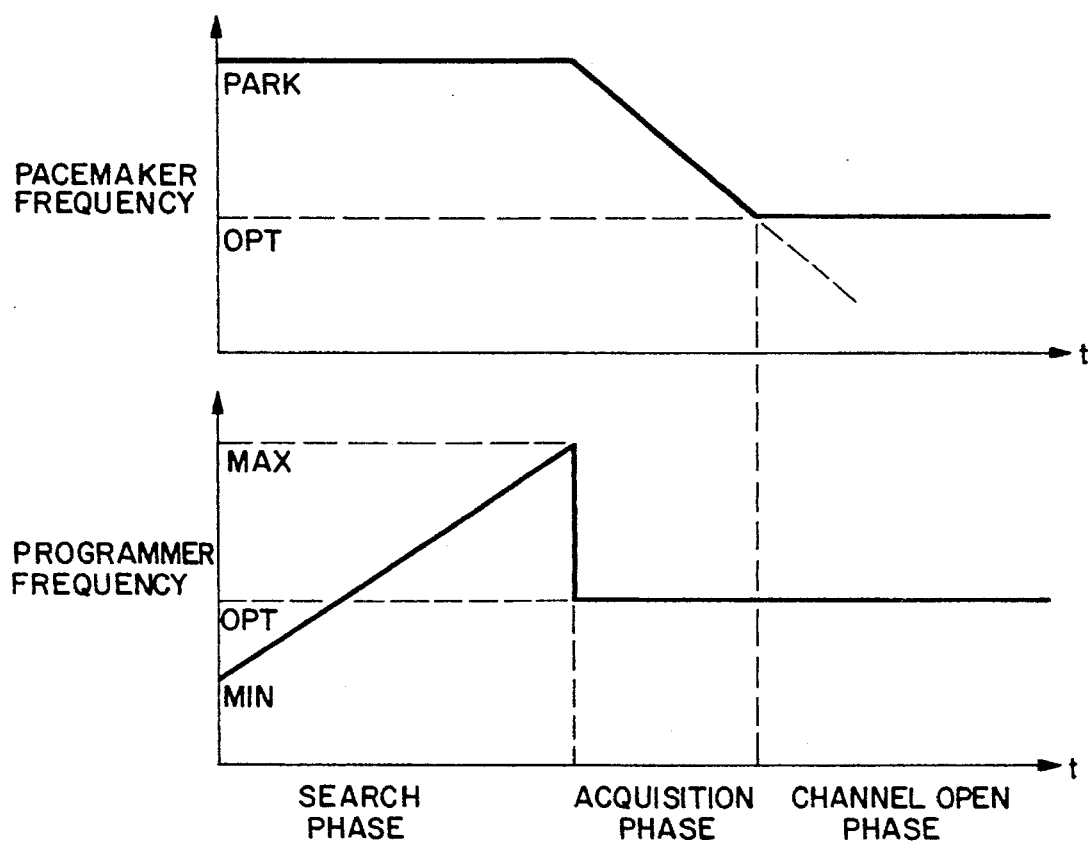
FIG. 3 is a timing diagram showing the sequence of operations followed by the implanted pacemaker and the external programmer in selecting an optimum telemetry frequency.

More particularly, the programmer 13 first determines the specific frequency within the fm broadcast band (88 MHz to 108 MHz) having the lowest ambient electromagnetic noise level. This specific frequency is considered the optimum frequency for telemetering the data. The determination of the optimum frequency is achieved by tuning the programmer's receiver 33 to a succession of frequencies that sweep across the band in small steps of, for example, 200 KHz. This frequency sweep is represented in FIG. 3 as the Search phase. At each frequency step, after an appropriate settling time, the receiver measures and stores in memory the strength of any received electromagnetic noise. During the time of this frequency sweep, the receiver 35 of the pacemaker 11 remains tuned at a predetermined park frequency that preferably is located at one end of the broadcast band, e.g., at 108 MHz.

After the receiver 33 of the programmer 13 has completed its full sweep of the fm band, it examines the successive noise measurements and selects as the optimum frequency the particular frequency having the lowest noise measurement. The programmer then conditions the pacemaker 11 to telemeter data at that optimum frequency by proceeding to an Acquisition phase (see FIG. 3). In this phase, the pacemaker repeatedly telemeters a predetermined start signal at a succession of frequencies that sweep across the fm band, in small steps of, for example, about 200 KHz.

This start signal is generated by a start signal generator 44 (FIG. 2), which is connected to the transmitter 25 via 44a.

The programmer 13 commands the pacemaker 11 to begin telemetering the start signal by transmitting a predetermined command signal to the pacemaker using the predetermined park frequency, which is the frequency at which the pacemaker's receiver 35 is then tuned. This command signal must be transmitted at a relatively high power level, in case extraneous noise is present at or near this park frequency and in case the frequency of the pacemaker's receiver might have been detuned from the nominal park frequency. The command signal is generated by the command generator 46 (FIG. 2), which is connected to the transmitter 37 of the programmer via line 46a, and it is detected by a command detector and mode controller 48, which is connected to the receiver 35 of the pacemaker via line 48a.

While the pacemaker's transmitter 25 performs its frequency sweep, the programmer's receiver 33 remains tuned to the optimum frequency that was previously determined. This is shown in FIG. 3. When the programmer's receiver eventually receives the telemetered start signal, it deduces that the pacemaker's frequency sweep has reached the optimum frequency. The command generator 46 thereupon commands the pacemaker 11, via the programmer's transmitter 37 and the pacemaker's receiver 35, to remain at that current frequency. This commanding can conveniently occur at the optimum frequency, because at that time both the programmer 13 and the pacemaker 11 are tuned to the optimum frequency.

Thereafter, the pacemaker 11 and the programmer 13 can communicate with each other at the optimum frequency, in a standard half-duplex fashion. In particular, during successive frames, the pacemaker's transmitter 25 can telemeter stored and/or real-time data at the optimum frequency, and the programmer's transmitter 37 can telemeter programming data, etc. at that same frequency, in an alternating fashion. This corresponds to the Channel Open phase in FIG. 3.

A full-duplex telemetry link, using two different frequencies, also could be provided, in a similar fashion. However, such a link is undesired for use with an implantable device such as a heart pacemaker, because it generally requires additional filters and power splitters.

Sometimes during the Channel Open phase, the signal-to-noise ratio can diminish to a point that data is no longer reliably received. When this happens, the programmer 13 can command the pacemaker 11, via the programmer's transmitter 37 and the pacemaker's receiver 35, to change its frequency to the park frequency, e.g., 108 MHz, and the preparatory procedure described above can be repeated so as to locate a new optimum frequency. This command from the programmer must be at a relatively high power level, so as to overcome whatever noise source has arisen. Alternatively, the programmer 13 can simply stop transmitting data, thereby inducing the pacemaker 11 to close the telemetry channel and return to the park frequency.

When the telemetry channel is closed, the receiver 35 of the pacemaker 11 should be in a park mode, in which it is tuned to the park frequency, and it should be awakened for short time durations at regular intervals, to sample any incoming commands from the transmitter 37 of the programmer 13. During this park mode, it is important that the receiver draw as little power as possible, so the duty cycle should be minimized. If, for example, the receiver is awakened for 10 microseconds every 500 milliseconds, and if the receiver draws 2 milliamps when it is on, then its average current would be only 40 nanoamps.

If, when the pacemaker's receiver 35 is briefly awakened, it detects a signal having greater than a predetermined minimum level, it will remain on for a longer time period and wait for a predetermined opening command. If the receiver fails to detect this opening command, it will return to its park mode. On the other hand, if the receiver does detect this opening command, it will immediately enter the Acquisition phase, as described above.

With reference again to FIG. 2, the frequency of the pacemaker's transmitter 25 and receiver 35 is made to be variable across the fm band by means of a varactor 45 connected in series with a dc blocking capacitor 47 and shunting the primary winding 27 of the transformer 29. The varactor provides a capacitance that varies according to its dc voltage drop, so that the application of a conventional staircase voltage waveform to the node 49 between the varactor and the dc blocking capacitor will cause the varactor's capacitance, and thus the transmitter's and receiver's frequency, to vary in a stepped fashion. The staircase voltage waveform is generated by a frequency selector 51, which is connected to the node 49 via line 51a.

It thus will be appreciated that the transmitter 25 and the receiver 35 of the pacemaker 11 are tuned to the optimum frequency without the need for the pacemaker to incorporate a crystal-controlled oscillator, or other elaborate frequency synthesizer, and without the need to draw excessive energy from the limited supply available so as to overcome any excessive interference at the operating frequency. Moreover, this optimal tuning can be achieved without the need to maintain long-term stability for the components of the pacemaker that control frequency. Limited drifts of those component values are permissible over time, because the tuning of the pacemaker effectively is under the control of the external programmer 13.

Although the invention has been described with reference only to the presently preferred embodiment, those skilled in the art will appreciate that various modifications can be made without departing from the invention. Accordingly, the invention is defined only by the following claims.

What is claimed is:

1. A method for establishing telemetry communication from an implantable device to an external device, comprising:

determining a particular optimum frequency within a predetermined frequency range, at which ambient electromagnetic noise from extraneous sources is at a low level;

transmitting from the implantable device a predetermined start signal, at a succession of frequencies within the predetermined frequency range;

tuning a receiver of the external device to the optimum frequency and monitoring received signals until the predetermined start signal has been received; and conditioning the implantable device, upon receipt by the external device of the predetermined start signal, to stop transmitting the start signal and to maintain its current frequency for further communications.

2. A method, as defined in claim 1, wherein determining a particular optimum frequency includes:

evaluating the frequency spectrum of ambient electromagnetic noise by sweeping the frequency of the receiver of the external device across the predetermined frequency range and measuring the strength of the received electromagnetic energy at each of a succession of discrete frequencies; and selecting as the optimum frequency the particular frequency at which the strength of the received electromagnetic energy is lowest.

3. A method, as defined in claim 1, wherein transmitting from the implantable device includes:

tuning a receiver of the implantable device to a predetermined park frequency within the predetermined frequency range; and transmitting a predetermined command signal from a transmitter of the external device to the receiver of the implantable device at the predetermined park frequency.

4. A method, as defined in claim 3, wherein transmitting from the implantable device further includes repeatedly transmitting the predetermined start signal at a succession of frequencies that sweeps uniformly across the predetermined frequency range, in discrete frequency steps.

5. A method for transmitting data between an implantable device and an external device, wherein the implantable device includes a transmitter and a receiver that operate at a selectable frequency located within a predetermined frequency range, and wherein the external device also includes a transmitter and a receiver that operate at a selectable frequency located within the same predetermined frequency range, comprising:

determining a particular optimum frequency within the predetermined frequency range at which ambient electromagnetic noise from extraneous sources is at a low level;

commanding the transmitter of the implantable device to transmit a predetermined start signal at a succession of frequencies within the predetermined frequency range;

tuning the receiver of the external device to the optimum frequency and monitoring the received signal until the predetermined start signal has been received, indicating that the transmitter of the implantable device is transmitting at the optimum frequency; and commanding the transmitter of the implantable device to transmit data at the frequency in use at the time the receiver of the external device has received the predetermined start signal.

6. A method for transmitting data, as defined in claim 5, wherein determining includes:

sweeping the frequency of the receiver of the external device across the predetermined frequency range and measuring the strength of the received electromagnetic energy at each of a succession of discrete frequencies; and selecting as the optimum frequency the particular frequency at which the strength of the received electromagnetic energy is lowest.

7. A method for transmitting data, as defined in claim 5, wherein the first step of commanding the transmitter of the implantable device includes:

tuning the receiver of the implantable device to a predetermined park frequency within the predetermined frequency range; and transmitting a predetermined command signal from the transmitter of the external device to the received of the implantable device at the predetermined park frequency.

8. A method for transmitting data, as defined in claim 5, wherein the first step of commanding includes commanding the transmitter of the implantable device to repeatedly transmit the predetermined start signal at a succession of frequencies that sweeps uniformly across the predetermined frequency range, in discrete frequency steps.

9. A method for transmitting data, as defined in claim 5, and further including a step of alternately transmitting data from the transmitter of the implantable device to the receiver of the external device and transmitting data from the transmitter of the external device to the receiver of the implantable device, using the optimum frequency.

10. A method for transmitting data, as defined in claim 5, wherein:

the implantable device further includes a varactor operatively associated with its transmitter and receiver, the varactor having a capacitance that affects the operating frequency of such transmitter and receiver; and the first step of commanding the transmitter includes generating a staircase voltage signal for application to the varactor.

11. Telemetry apparatus comprising:

an implantable device including a transmitter and a receiver that operate at a selectable frequency located within a predetermined frequency range; and an external device including a transmitter and a receiver that operate at a selectable frequency within the predetermined frequency range;

wherein the external device includes first means for sweeping the frequency of its receiver through the predetermined frequency range and for determining a particular optimum frequency at which ambient electromagnetic noise from extraneous sources is at a low level;

wherein the external device further second means for causing its transmitter to transmit a command to the implantable device, to command the transmitter of the implantable device to transmit a predetermined start signal at a succession of frequencies within the predetermined frequency range, while the receiver of the external device remains tuned to the optimum frequency, awaiting receipt of the predetermined start signal;

and wherein the external device further includes third means for causing the transmitter of the external device, upon receipt of the predetermined start signal by the receiver of the external device, to transmit a command to the implantable device, to command the transmitter of the implantable device to thereafter transmit data at the frequency then in use.

12. Telemetry apparatus, as defined in claim 11, wherein the first means of the external device sweeps the frequency of the receiver of the external device across the predetermined frequency range and measures the strength of the received electromagnetic energy at each of a succession of discrete frequencies and selects as the optimum frequency the particular frequency at which the strength of the received electromagnetic energy is lowest.

13. Telemetry apparatus, as defined in claim 11, wherein:

the implantable device includes means for tuning its receiver to a frequency at or near a predetermined park frequency within the predetermined frequency range; and the transmitter of the external device commands the implantable device to begin transmitting the predetermined successive start signals by transmitting a predetermined command signal at the predetermined park frequency.

14. Telemetry apparatus, as defined in claim 11, wherein the implantable device includes means for transmitting the predetermined start signal at a succession of frequencies that sweeps uniformly across the predetermined frequency range, in discrete frequency steps.

15. Telemetry apparatus, as defined in claim 11, wherein the implantable device and the external device further include means for alternately transmitting data from the transmitter of the implantable device to the receiver of the external device and for transmitting data from the transmitter of the external device to the receiver of the implantable device, using the optimum frequency.

16. Telemetry apparatus, as defined in claim 11, wherein:

the implantable device further includes a varactor operatively associated with its transmitter and receiver; and the implantable device further includes means for generating a staircase voltage signal for application to the varactor, to sweep the frequency of its transmitter and receiver through the predetermined frequency range in a stepwise fashion.

17. Telemetry apparatus, as defined in claim 11, wherein the implantable device is free of a crystal-controlled oscillator for use in association with its transmitter and receiver.

* * * * *